United States Patent [19]

McEver

[11] Patent Number: 5,198,424
[45] Date of Patent: Mar. 30, 1993

[54] FUNCTIONALLY ACTIVE SELECTIN-DERIVED PEPTIDES

[75] Inventor: Rodger P. McEver, Oklahoma City, Okla.

[73] Assignee: Board of Regents of the University of Oklahoma, Norman, Okla.

[21] Appl. No.: 867,271

[22] Filed: Apr. 7, 1992

Related U.S. Application Data

[63] Continuation of Ser. No. 554,199, Jul. 17, 1990, abandoned, which is a continuation-in-part of Ser. No. 320,408, Mar. 8, 1989.

[51] Int. Cl.$^5$ ............... A61K 37/00; A61K 43/00; C07K 5/00; C07K 7/00
[52] U.S. Cl. ............... 514/13; 514/12; 514/14; 514/15; 514/16; 530/324; 530/325; 530/326; 530/327; 424/1.1; 623/11
[58] Field of Search ............... 514/12, 13, 14, 15, 514/16; 530/324, 327, 325; 424/328, 326, 1.1; 623/11

[56] References Cited

PUBLICATIONS

Lasky et al., Cell, vol. 56, Mar. 24, 1989, pp. 1045–1055.
Gamble et al., Science, vol. 249, Jul. 27, 1990, pp. 414–417.
Johnston et al, (J. Biol. Chem.), vol. 265, No. 34, Dec. 5, 1990, pp. 21381–21385.
Issekutz et al., vol. 49, No. 6, Laboratory Investigation, 1983, pp. 716–724.
Johnston et al, Cell, vol. 56, Mar. 24, 1989, pp. 1033–1044.
McEver, R., et al., J. Biol. Chem., vol. 259, No. 15, pp. 9799–9804 (Aug. 10, 1984).
Stenberg, P., et al., J. Cell. Biol., vol. 101, pp. 880–886 (Sep. 1985).
McEver, et al., Blood 70(5) Suppl. 1:355a, Abstract No. 1274 (1987).
Johnston, et al., Blood 70(5) Suppl. 1:352a Abstract No. 1264 (1987).
Muller-Eberhard, H., Ann. Rev. Biochem. 57:321–347 (1988).
Bevilacqua, M. P., et al., Science, vol. 243, pp. 1160–1165 (Mar. 3, 1989).
Siegelman, M. H., et al., Science, vol. 243, pp. 1165–1172 (Mar. 3, 1989).
Larsen, E., et al., Cell, vol. 59, 305–312 (Oct. 20, 1989).
Hamburger, S., et al., Blood, vol. 75, No. 3, pp. 550–554 (Feb. 1, 1990).
Brandley, B. K., et al., Cell, vol. 63, 861–863 (Nov. 30, 1990).
Springer, T. A., et al., Nature, vol. 349, pp. 196–197, (Jan. 17, 1991).
Goelz, S. E., et al., Cell, vol. 63, pp. 1349–1356 (Dec. 21, 1990).
Corral, L., et al., Biochem. & Biophy. Res. Comm., vol. 172, No. 3, pp. 1349–1356 (Nov. 15, 1990).
Tiemeyer, M., et al., Proc. Natl. Acad. Sci., vol. 88, pp. 1138–1142 (Feb. 1991).

(List continued on next page.)

Primary Examiner—Merrell C. Cashion, Jr.
Assistant Examiner—A. M. Davenport
Attorney, Agent, or Firm—Kilpatrick & Cody

[57] ABSTRACT

Peptides derived from three regions of the lectin binding region of GMP-140 have been found to selectively interact with "selectins", including GMP-140, ELAM-1, and lymphocyte homing receptor. The peptides can be as short as eight to thirteen amino acids in length and are easily prepared and modified by standard techniques. Critical elements of the counter-receptor or ligand on the neutrophils which binds GMP-140 are also identified. The peptides are useful as diagnostics and, in combination with a suitable pharmaceutical carrier, for clinical applications in the modulation or inhibition of coagulation processes or inflammatory processes.

7 Claims, 5 Drawing Sheets

PUBLICATIONS

Lowe, J. B., et al., *Cell*, vol. 63, pp. 475–484 (Nov. 2, 1990).

Walz, G., et al., *Science*, vol. 250, pp. 1132–1135 (Nov. 23, 1990).

Phillips, M. L., et al., *Science* vol. 250, pp. 1130–1131 (Nov. 23, 1990).

Bowen, B. R., et al., *J. of Cell Biol.*, vol. 109, pp. 421–427 (Jul. 1989).

Siegelman, M. H., et al., *Proc. Natl. Acad. Sci.*, vol. 86, pp. 5562–5566 (Jul. 1989).

Tedder, T., et al., *J. Exp. Med.*, vol. 170, pp. 123–133 (Jul. 1989).

Hourcade, D., et al., *Advances in Immunology*, vol. 45, pp. 381–415 (1989).

Larsen, E., et al., *Cell*, vol. 59, pp. 305–312 (Oct. 20, 1989).

Watson, M. L., et al., *J. Exp. Med.*, vol. 172, pp. 263–271 (Jul. 1990).

Hattori, R., et al., *J. Biol. Chem.*, vol. 264, No. 15, pp. 9053–9060 (1989).

Patel, K. D., et al., *J. of Cell Biol.*, vol. 112, No. 4, pp. 749–759 (Feb. 1991).

Bonfanti, R.. et al. *Blood*, vol. 73, No. 5, pp. 1109–1112 (Apr. 1989).

Hattori, R., et al., *J. of Biol. Chem.*, vol. 264, No. 14, pp. 7768–7771 (May 15, 1989).

McEver, R., et al., *J. Clin. Invest.*, vol. 84, pp. 92–99 (Jul. 1989).

Skinner, M. P., et al., *Biochem. & Biophys. Res. Comm.*, vol. 164, pp. 1373–1379 (1989).

Geng, J-G., et al., *Nature*, vol. 343, No. 6260, pp. 757–760 (Feb. 22, 1990).

Larsen, E., et al., *Cell*, vol. 63, pp. 467–474, (Nov. 2, 1990).

FUNCTIONALLY ACTIVE SELECTIN-DERIVED PEPTIDES

The U.S. Government has rights in this invention by virtues of grants from the National Heart, Lung and Blood Institute.

This is a continuation of copending application Ser. No. 07/554,199 filed on Jul. 17, 1990 abandoned, which is a continuation-in-part of U.S. Ser. No. 07/320,408 entitled "Method for Modulation of Inflammatory Responses" filed Mar. 8, 1989 by Rodger P. McEver.

BACKGROUND OF THE INVENTION

This invention is generally in the field of methods for the treatment and prevention of inflammatory responses involving binding reactions with selections including GMP-140, ELAM-1, and lymphocyte-homing receptor.

The adherence of platelets and leukocytes to vascular surfaces is a critical component of the inflammatory response, and is part of a complex series of reactions involving the simultaneous and interrelated activation of the complement, coagulation, and immune systems.

The complement proteins collectively play a leading role in the immune system, both in the identification and in the removal of foreign substances and immune complexes, as reviewed by Muller-Eberhard, H. J., *Ann. Rev. Biochem.* 57:321-347 (1988). Central to the complement system are the C3 and C4 proteins, which when activated covalently attach to nearby targets, marking them for clearance. In order to help control this process, a remarkable family of soluble and membrane-bound regulatory proteins has evolved, each of which interacts with activated C3 and/or C4 derivatives. The coagulation and inflammatory pathways are regulated in a coordinate fashion in response to tissue damage. For example, in addition to becoming adhesive for leukocytes, activated endothelial cells express tissue factor on the cell surface and decrease their surface expression of thrombomodulin, leading to a net facilitation of coagulation reactions on the cell surface. In some cases, a single receptor can be involved in both inflammatory and coagulation processes.

Leukocyte adherence to vascular endothelium is a key initial step in migration of leukocytes to tissues in response to microbial invasion. Although a class of inducible leukocyte receptors, the CD11-CD18 molecules, are thought to have some role in adherence to endothelium, mechanisms of equal or even greater importance for leukocyte adherence appear to be due to inducible changes in the endothelium itself.

Activated platelets have also been shown to interact with both neutrophils and monocytes in vitro. The interaction of platelets with monocytes may be mediated in part by the binding of thrombospondin to platelets and monocytes, although other mechanisms have not been excluded. The mechanisms for the binding of neutrophils to activated platelets are not well understood, except that it is known that divalent cations are required. In response to vascular injury, platelets are known to adhere to subendothelial surfaces, become activated, and support coagulation. Platelets and other cells may also play an important role in the recruitment of leukocytes into the wound in order to contain microbial invasion.

Endothelium exposed to "rapid" activators such as thrombin and histamine becomes adhesive for neutrophils within two to ten minutes, while endothelium exposed to cytokines such as tumor necrosis factor and interleukin-1 becomes adhesive after one to six hours. The rapid endothelial-dependent leukocyte adhesion has been associated with expression of the lipid mediator platelet activating factor (PAF) on the cell surface, and presumably, the appearance of other endothelial and leukocyte surface receptors. The slower cytokine-inducible endothelial adhesion for leukocytes is mediated, at least in part, by an endothelial cell receptor, ELAM-1, that is synthesized by endothelial cells after exposure to cytokines and then transported to the cell surface, where it binds neutrophils. The isolation, characterization and cloning of ELAM-1 is reviewed by Bevilacqua, et al., in *Science* 243, 1160-1165 (1989). A peripheral lymph node homing receptor, also called "the murine Mel 14 antigen", "Leu 8", the "Leu 8 antigen" and "LAM-1", is another structure on neutrophils, monocytes, and lymphocytes that binds lymphocytes to high endothelial venules in peripheral lymph nodes. The characterization and cloning of this protein is reviewed by Lasky, et al., *Cell* 56, 1045-1055 (1989) (mouse) and Tedder, et al., *J. Exp. Med.* 170, 123-133 (1989).

GMP-140 (granule membrane protein 140), also known as PADGEM, is a cysteine-rich and heavily glycosylated integral membrane glycoprotein with an apparent molecular weight of 140,000 as assessed by sodium dodecyl sulfate polyacrylamide gel electrophoresis (SDS-PAGE). GMP-140 was first purified from human platelets by McEver and Martin, *J. Biol. Chem.* 259:9799-9804 (1984). The protein is present in alpha granules of resting platelets but is rapidly redistributed to the plasma membrane following platelet activation, as reported by Stenberg, et al., (1985). The presence of GMP-140 in endothelial cells and its biosynthesis by these cells was reported by McEver, et al., *Blood* 70(5) Suppl. 1:355a, Abstract No. 1274 (1987). In endothelial cells, GMP-140 is found in storage granules known as the Weibel-Palade bodies. GMP-140 (called PADGEM) has also been reported to mediate the interaction of activated platelets with neutrophils and monocytes by Larsen, et al., in *Cell* 59, 305-312 (October 1989) and Hamburger and McEver, *Blood* 75:550-554 (1990).

The cDNA-derived amino acid sequence, reported by Johnston, et al., in *Cell* 56, 1033-1044 (Mar. 24, 1989), and in U.S. Ser. No. 07/320,408 filed Mar. 8, 1989, indicates that it contains a number of modular domains that are likely to fold independently. Beginning at the N-terminus, these include a "lectin" domain, an "EGF" domain, nine tandem consensus repeats similar to those in complement binding proteins, a transmembrane domain (except in a soluble form that appears to result from differential splicing), and a cytoplasmic tail.

When platelets or endothelial cells are activated by mediators such as thrombin, the membranes of the storage granules fuse with the plasma membrane, the soluble contents of the granules are released to the external environment, and membrane bound GMP-140 is presented within seconds on the cell surface. The rapid redistribution of GMP-140 to the surface of platelets and endothelial cells as a result of activation suggests that this glycoprotein could play an important role at sites of inflammation or vascular disruption.

ELAM-1, the homing receptor, and GMP-140 have been termed "selectins", based on their related structure and function.

The in vivo significance of platelet-leukocyte interactions has not been studied carefully. However, in response to vascular injury, platelets are known to adhere to subendothelial surfaces, become activated, and support coagulation. Platelets and other cells may also play an important role in the recruitment of leukocytes into the wound in order to contain microbial invasion. Conversely, leukocytes may recruit platelets into tissues at sites of inflammation, as reported by Issekutz, et al., *Lab. Invest.* 49:716 (1983).

The coagulation and inflammatory pathways are regulated in a coordinate fashion in response to tissue damage. For example, in addition to becoming adhesive for leukocytes, activated endothelial cells express tissue factor on the cell surface and decrease their surface expression of thrombomodulin, leading to a net facilitation of coagulation reactions on the cell surface. In some cases, a single receptor can be involved in both inflammatory and coagulation processes.

Proteins involved in the hemostatic and inflammatory pathways are of interest for diagnostic purposes and treatment of human disorders. However, there are many problems using proteins therapeutically. Proteins are usually expensive to produce in quantities sufficient for administration to a patient. Moreover, there can be a reaction against the protein after it has been administered more than once to the patient. It is therefore desirable to develop peptides having the same, or better, activity as the protein, which are inexpensive to synthesize, reproducible and relatively innocuous.

It is therefore an object of the present invention to provide peptides having activity of selectins, including GMP-140, ELAM-1, and lymphocyte homing receptor.

It is another object of the present invention to provide methods for using these peptides to inhibit leukocyte adhesion to endothelium or to platelets.

It is a further object of the present invention to provide methods for using these peptides to modulate the immune response and the hemostatic pathway.

It is yet another object of the present invention to provide peptides for use in diagnostic assays relating to GMP-140, ELAM-1, and lymphocyte homing receptor.

It is yet another object of the present invention to provide carbohydrate-based reagents, based on the structure of the leukocyte ligand for GMP-140, to inhibit GMP-140 - mediated adhesive interactions.

SUMMARY OF THE INVENTION

Peptides derived from three regions of the lectin binding region of GMP-140 have been found to function as "selectins", including GMP-140, ELAM-1, and lymphocyte homing receptor. The three regions include amino acids 19-34, 54-72, and 66-89, based on the numbers of the residues contained in the peptide, with residue 1 defined as the N terminus of the mature protein after cleavage of the signal peptide. The peptides can be as short as eight to thrirteen amino acids in length and are easily prepared by standard techniques. They can also be modified to increase in vivo half-life, by chemical modification of the amino acids or by attachment to a carrier molecule or inert substrate. Critical elements of the counter-receptor or ligand on the neutrophils which binds GMP-130 are also identified.

Examples demonstrate that the peptides bind neutrophils and inhibit binding of GMP-140 to neutrophils, with an $IC_{50}$ (the dose required to inhibit adhesion of neutrophils to immobilized GMP-140 by 50%) ranging from 50 to 300 micromolar. The binding affinity can be modulated using sequences from the EGF domain and divalent cations which bind to both the EGF and lectin domains. An assay is also demonstrated that is useful for screening for variations of these peptides that interfere with binding of all selectins or individual selectins, especially GMP-140.

The peptides are useful as diagnostics and, in combination with a suitable pharmaceutical carrier, for clinical applications in the modulation or inhibition of coagulation processes or inflammatory processes.

BRIEF DESCRIPTION OF THE DRAWINGS

FIG. 1 is the nucleotide and deduced amino acid sequence of endothelial cell GMP-140. The translated amino acid sequence of the open reading frame is given in the single-letter code. The stop codon is shown by the asterisk. The thin underlines show the matching positions of amino acid sequences determined from the N-terminus and from 26 peptides of platelet GMP-140. The signal peptide corresponds to positions -41 to -1. The putative transmembrane domain is heavily underlined. The cysteine residues are circled and potential asparagine-linked glycosylation sites (NXS/T) are shown by the dark circles. Two potential polyadenylation signals in the 3' untranslated region are underlined and overlined. This figure is from U.S. Ser. No. 07/320,408.

DETAILED DESCRIPTION OF THE INVENTION

The structure and biosynthesis of GMP-140 has now been analyzed in detail. The entire amino acid sequence of GMP-140 has been determined by a combination of protein sequencing of peptide fragments derived from purified platelet GMP-140 and by cloning of cDNAs encoding GMP-140 from a human endothelial cell cDNA library. Based on the structure and on functional studies, GMP-140 acts as a receptor for neutrophils, and interacts with complement protein C3b and the anticoagulant cofactor protein S.

THE CDNA AND AMINO ACID SEQUENCE OF GMP-140

Cloning of the gene for GMP-140 was first reported by G. I. Johnston, R. G. Cook and R. P. McEver in Abstract 1238 Supplement II *Circulation* 78(4) (October 1988). Oligonucleotides were prepared based on N-terminal amino acid sequencing of GMP-140 peptides and used to screen a human endothelial cell cDNA library. A 3.0 kb clone was isolated which encoded a protein of 727 amino acids. An N-terminal domain of 118 residues containing many cysteines, lysines, and tyrosines, which is similar to the asialo glycoprotein receptor, is followed by an EGF-type repeating domain structure, and eight tandem repeats of 62 amino acids each, except for the sixth tandem repeat which has 70 amino acids. The repeats are homologous to those found in a family of proteins that include proteins regulating C3b and C4b, but are unique in having six conserved cysteines per repeat instead of the typical four. These are followed by a 24 amino acid transmembrane region and a 35 amino acid cytoplasmic tail. There appear to be at least two forms of the protein derived by alternative splicing of transcripts of the same gene: a soluble form and a membrane or granule bound form.

Figure 1:
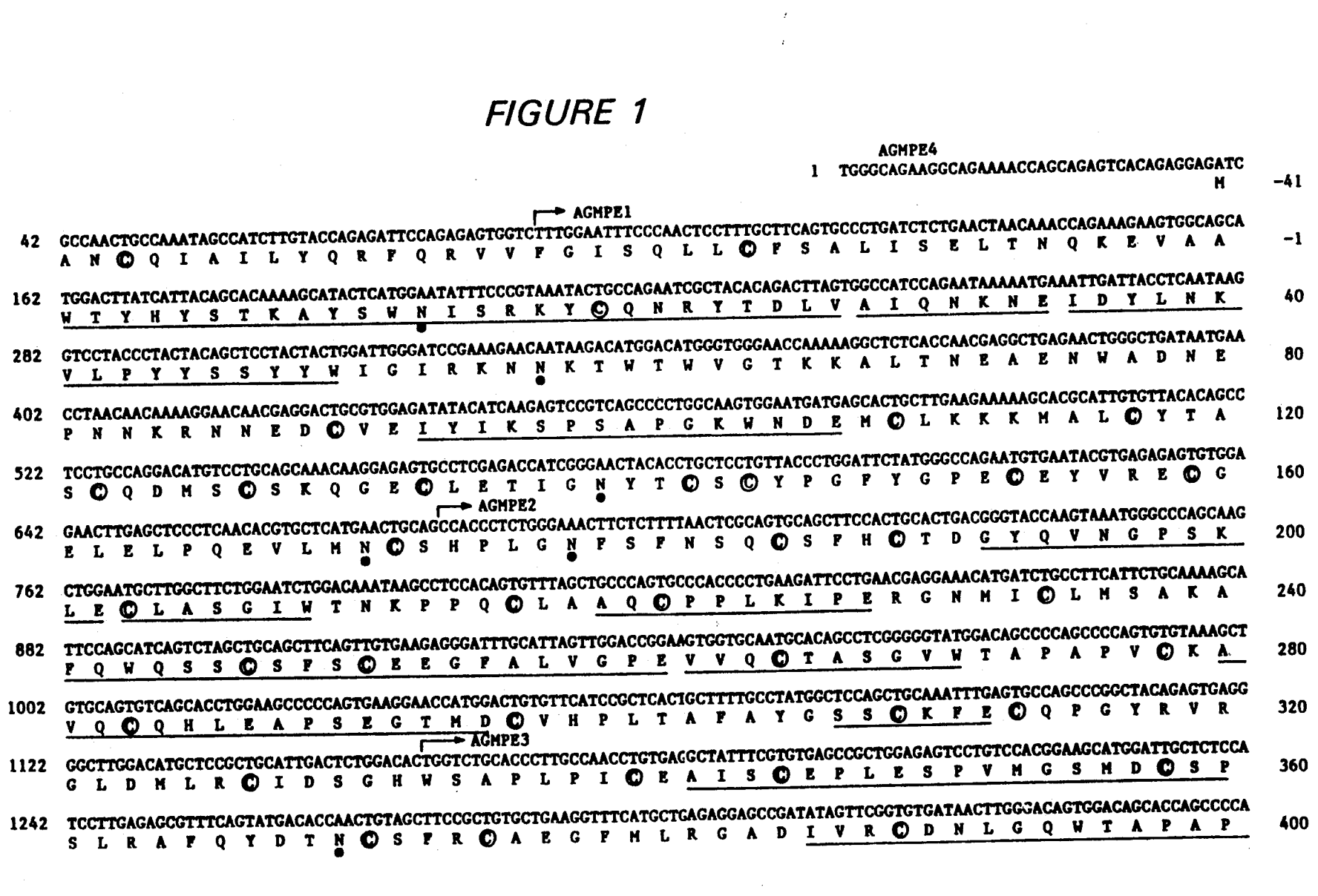
Figure 1:
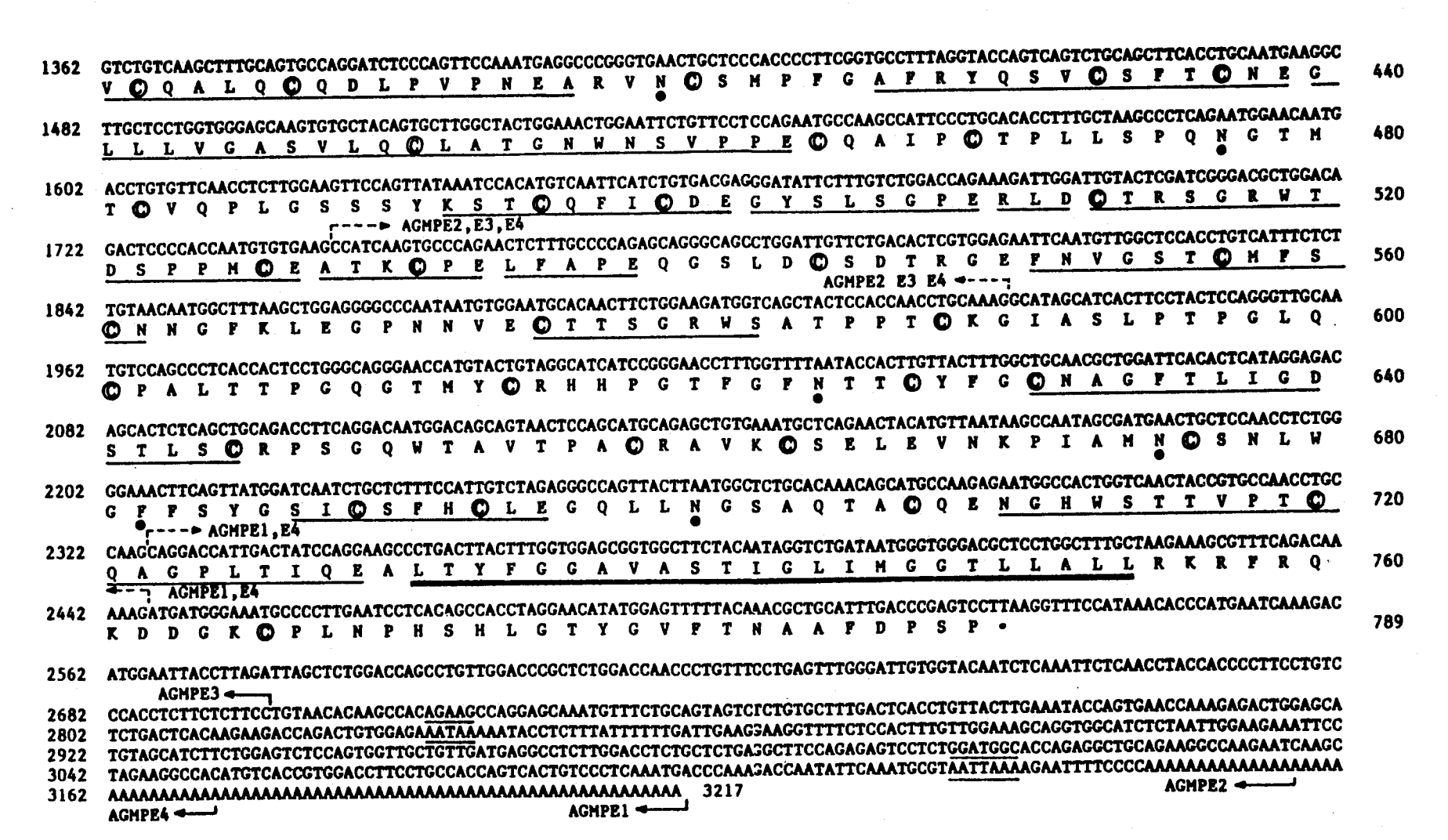
Figure 2:
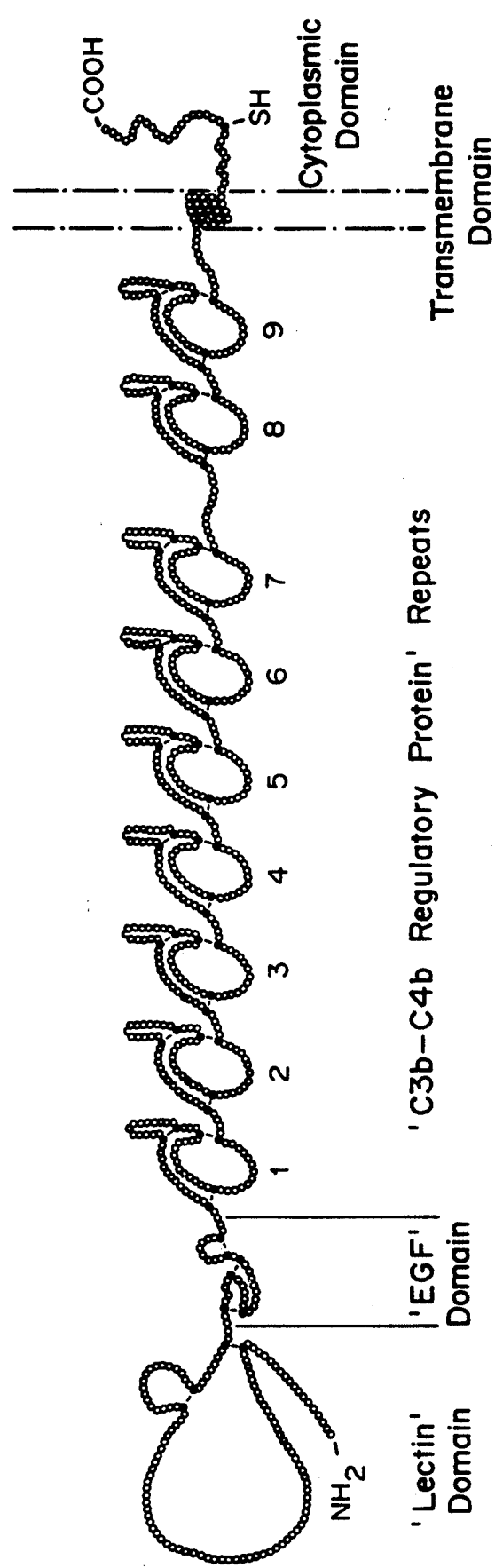
FIG. 2 is the proposed folding pattern of the domains in GMP-140. The cysteine residues are shown by the dark circles and the potential free sulfhydryl in the cytoplasmic domain is indicated by —SH. This figure is from U.S. Ser. No. 07/320,408.

The predicted amino acid sequence of endothelial cell GMP-140, shown in FIG. 1, suggests the presence of six different structural domains, shown schematically in FIG. 2. One of these regions, a 24-residue hydrophobic segment near the C-terminus, is characteristic of membrane spanning domains. Most of the protein is located on the N-terminal side of this domain and appears to be extracytoplasmic, i.e., facing the lumen of the secretory granule, or, following activation of the cell, exposed to the extracellular environment.

Beginning at the N-terminus, the first domain contains 41 residues (labeled -41 to -1 in FIG. 1) and has the characteristic features of a signal peptide. These include several positively charged amino acids, followed by a hydrophobic domain and then a region rich in polar residues. The small uncharged residues found at positions -3 and -1 are typical of those found at sites of cleavage by signal peptidase. In addition, the amino acid sequence of the N-terminus of platelet GMP-140 matches the deduced endothelial cell sequence at 25 out of 27 positions from residues 1 to 27.

Following the signal peptide, the translated cDNA sequence predicts a mature protein of 789 residues. Comparison of the sequences of platelet GMP-140 peptides to the deduced endothelial cell sequence showed that 337 of 341 assigned amino acids match, suggesting that both cell types synthesize the same protein.

There are 12 potential asparagine-linked glycosylation sites having the consensus sequence NxS/T. All are located on the extracytoplasmic portion of the molecule and all appear to be glycosylated based on the carbohydrate composition of platelet GMP-140. The mature protein contains 65 cysteines accounting for 8% of the total amino acids. Most of these are predicted to be organized into disulfide bridges since only a small amount of carboxymethyl cysteine can be identified in samples of nonreduced GMP-140 treated with iodoacetamide.

The second domain begins at residue 1 and encompasses the first 118 amino acids of the mature protein. This region is rich in lysine (12%), tyrosine (10%), asparagine (13%), and tryptophan (6%) residues. This region of GMP-140 is designated as a "lectin" domain, since many of the proteins containing this motif bind carbohydrate.

The third domain, which begins at residue 119, has a sequence of 40 amino acids that contains six cysteines. Comparison of this region of GMP-140 to sequences in the NBRF database reveals many proteins that contain the same arrangement of cysteines. The first protein described with this motif is the epidermal growth factor (EGF) precursor, which contains ten homologous copies (Gray, et al., *Nature* 303:236–240 (1983; Scott, et al., Nature 221:236–240 (1983).

The fourth domain, which begins at residue 159, consists of nine tandem consensus repeats, each containing 62 amino acids; in addition, extensions of eight and four residues, respectively, are found at the ends of the seventh and ninth repeats. The boundaries of this domain are set arbitrarily at the first cysteine of the initial repeat and at the last residue before the putative transmembrane domain. A consensus sequence shows that many amino acids occur in at least five out of the nine repeats. All repeats contain six conserved cysteines, three glycines, and one tryptophan, phenylalanine, proline, and leucine. The cysteine residues are arranged in a different motif than the six cysteines found in the "EGF" domain. The repeats are 31% to 56% identical to each other at the amino acid level and 42% to 62% identical at the nucleotide level. No gaps are required to maximize the alignment among the repeats.

The fifth domain, beginning at residue 731, is the 24-residue putative transmembrane domain. Following this is the sixth domain, a presumed cytoplasmic segment of 35 residues that begins with several highly charged residues and ends at the C-terminus of the protein at residue 789. There are possible phosphorylation sites at serine, threonine, and tyrosine residues, as well as a cysteine that might undergo posttranslational modification.

Two different in-frame deletions are identified among the sequences of the four endothelial-cell clones examined in detail. The first deletion is 186 bp. This deletion removes 62 amino acids from the seventh consensus repeat and predicts a protein containing eight instead of nine repeats. The second deletion is 120 bp, which removes 40 amino acids just after the end of the ninth repeat. The region deleted includes the transmembrane domain and the first few residues of the cytoplasmic domain. The remaining 28 residues at the C-terminus are predicted to continue just after the ninth repeat. A hydrophilicity plot (Kyte and Doolittle, *J.Mol.Biol.* 157:105–132 (1982) predicts that this form of GMP-140 is soluble.

GMP-140 has been demonstrated to be a receptor on platelets and endothelial cells that binds to a surface ligand on neutrophils and monocytes, thereby facilitating the inflammatory process.

The conclusion that GMP-140 serves as receptor for the adherence of leukocytes to activated endothelial cells and platelets was originally based on several observations: the rapid appearance of GMP-140 on the surface of endothelium stimulated with thrombin or histamine which parallels the inducible adherence of neutrophils to endothelium stimulated with these agonists; the interaction of neutrophils or monocytes with platelets only after platelet activation with agonists such as thrombin which cause redistribution of GMP-140 to the cell surface and not with platelet agonists such as ADP; concentration of GMP-140 in postcapillary venules which are the predominant sites for binding of leukocytes to endothelium prior to their migration across the endothelium into the tissues; specific adherence of purified neutrophils to GMP-140 coated on tissue culture microtiter wells; blocking by polyclonal antibodies to GMP-140 of 60-90%, of the adherence of neutrophils to cultured human umbilical vein endothelial cells stimulated with histamine; similarity of the cDNA-derived amino acid sequence of GMP-140 to that of ELAM-1, an endothelial cell protein already known to bind neutrophils, and to lymphocyte homing receptor. Subsequent studies have demonstrated that GMP-140 also mediates adhesion of neutrophils to stimulated platelets, but not unstimulated platelets, in the presence of $Ca^{2+}$. The binding of platelets to neutrophils was inhibited by a monoclonal antibody to GMP-140 and by purified GMP-140.

Other studies have demonstrated that GMP-140 binds to C3b, a complement system protein, and protein S, an anticoagulant cofactor protein. GMP-140 shares sequence homology with the plasma protein C4b-binding protein (C4bp), which not only interacts with the plasma protein C4b but also with protein S.

PEPTIDES DERIVED FROM THE LECTIN DOMAIN OF GMP-140 WHICH COMPETE WITH GMP-140 FOR BINDING OF NEUTROPHILS

Peptides derived from GMP-140 have now been discovered that are useful in diagnostics and in modulating the hemostatic and inflammatory responses in a patient wherein a therapeutically effective amount of a peptide capable of blocking leukocyte recognition of GMP-140 is administered to the patient.

It has now been discovered that peptide sequences within the lectin domain of GMP-140, having homology with the lectin domains of other proteins, especially ELAM-1 and the homing receptor, selectively inhibit neutrophil adhesion to purified GMP-140, can therefore be used in diagnostic assays of patients and diseases characterized by altered binding by these molecules, and in screening assays for compounds altering this binding, and should be useful clinically to inhibit or modulate interactions of leukocytes with platelets or endothelial cells involving coagulation and/or inflammatory processes.

The cDNA-derived primary structure of GMP-140 provides several insights into functions for GMP-140 in the vascular system. The most remarkable observation is the striking structural similarity of GMP-140 to two other receptors found on vascular cells which have been recently cloned.

The first of these similar receptors is ELAM-1. ELAM-1 is an endothelial cell protein that is not present in unstimulated endothelium. However, when endothelium is exposed to cytokines such as tumor necrosis factor or interleukin-1, the gene for ELAM-1 is transcribed, producing RNA which in turn is translated into protein. The result is that ELAM-1 is expressed on the surface of endothelial cells 1-4 hours after exposure to cytokines, as reported by Bevilacqua et al., *Proc.Natl.Acad.Sci.USA* 84:9238-9242 (1987) (in contrast to GMP-140, which is stored in granules and presented on the cell surface within seconds after activation). ELAM-1 has been shown to mediate the adherence of neutrophils to cytokine-treated endothelium and thus appears to be important in allowing leukocytes to migrate across cytokine-stimulated endothelium into tissues. The cDNA-derived primary structure of ELAM-1 indicates that it contains a "lectin" domain, an EGF domain, and six (instead of the nine in GMP-140) repeats similar to those of complement-regulatory proteins, a transmembrane domain, and a short cytoplasmic tail. There is extensive sequence homology between GMP-140 and ELAM-1 throughout the both proteins, but the similarity is particularly striking in the lectin and EGF domains.

The second molecule with overall structural similarity to GMP-140 is a homing receptor found on lymphocytes. Homing receptors are lymphocyte surface structures that allow lymphocytes to bind to specialized endothelial cells in lymphatic tissues, termed high endothelial cells or high endothelial venules (reviewed by Yednock and Rose, *Advances in Immunology*. vol. 44, F. I. Dixon,ed., 313-378 (Academic Press, New York 1989). This binding allows lymphocytes to migrate across the endothelium into the lymphatic tissues where they are exposed to processed antigens. The lymphocytes then re-enter the blood through the lymphatic system. The homing receptor contains a lectin domain, an EGF domain, two complement-binding repeats, a transmembrane domain, and a short cytoplasmic tail. The homing receptor also shares extensive sequence homology with GMP-140, particularly in the lectin and EGF domains.

A comparison of the lectin domains between GMP-140, ELAM-1, and the homing receptor (LEU-8) is shown in Table I. Based on these sequence similarities it should be possible to select those peptides inhibiting binding of neutrophils to GMP-140 which will inhibit binding of ELAM-1, the homing receptor, and other homologous selectins, to components of the inflammatory process, or, conversely, which will inhibit only GMP-140 binding.

EXAMPLE 1: DEMONSTRATION OF COMPETITIVE INHIBITION OF BINDING OF NEUTROPHILS TO IMMOBILIZED GMP-140 BY PEPTIDES FROM THE LECTIN DOMAIN OF GMP-140

The role of the GMP-140 lectin domain was tested by synthesizing a series of peptides spanning almost all of the 118 residues of the lectin domain, except for two hydrophobic stretches predicted to be sequestered in the interior of the molecule. Peptides were also synthesized encompassing the EGF-like domain (36 residues) which follows the lectin domain. Peptides were also made from one of the consensus repeats, the transmembrane region, and the C-terminus (cytoplasmic tail) of the molecule as controls. Active peptides derived from the lectin domain are shown in Table I which also aligns the related sequences of the lectin domains of ELAM-1 and the homing receptor, LEU-8. Peptides were prepared either on an Applied Biosystems Model 430A automated peptide synthesizer using t-Boc chemistry or on a Dupont RAMPS manual peptide synthesizer using Fmoc chemistry. After cleavage from the resin on which they were synthesized, all peptides were purified by reverse phase high performance liquid chromatography.

Peptides were screened for their ability to inhibit neutrophil adhesion to purified GMP-140 immobilized on plastic wells, using the assay described by Geng, et al., *Nature* 343, 757-760 (1990).

Human neutrophils are isolated from heparinized whole blood by density gradient centrifugation on Mono-Poly resolving media, Flow Laboratories. Neutrophil suspensions are greater than 98% pure and greater than 95% viable by trypan blue exclusion. For adhesion assays, neutrophils are suspended at a concentration of $2 \times 10^6$ cells/ml in Hanks' balanced salt solution containing 1.26 mM $Ca^{2+}$ and 0.81 mM $Mg^{2+}$ (HBSS, Gibco) with 5 mg/ml human serum albumin (HBSS/HSA). Adhesion assays are conducted in triplicate in 96-well microtiter plates, Corning, incubated at 4° C. overnight with 50 microliters of various protein solutions.

GMP-140 is isolated from human platelet lysates by immunoaffinity chromatography on antibody S12-Sepharose TM and ion-exchange chromatography on a Mono-Q TM column (FLPC, Pharmacia Fine Chemicals), as follows.

Outdated human platelet packs (100 units) obtained from a blood bank and stored at 4° C. are pooled, adjusted to 5 mM EDTA at pH 7.5, centrifuged at 4,000 rpm for 30 min in 1 liter bottles, then washed three times with 1 liter of 0.1 M NaCl, 20 mM Tris pH 7.5 (TBS), 5 mM EDTA, 5 mM benzamidine.

The pellets are then resuspended in a minimum amount of wash buffer and made 1 mM in DIFP, then frozen in 50 ml screwtop tubes at $-80°$ C.

The frozen platelets are thawed and resuspended in 50 ml TBS, 5 mM benzamidine, 5 mM EDTA pH 7.5, 100 M leupeptin. The suspension is frozen and thawed two times in a dry ice-acetone bath using a 600 ml lyophilizing flask, then homogenized in a glass/teflon mortar and pestle and made 1 mM in DIFP. The NaCl concentration is adjusted to 0.5 M with a stock solution of 4 M NaCl. After stirring the suspension at 4° C., it is centrifuged in polycarbonate tubes at 33,000 rpm for 60 min at 4° C. The supernatant (0.5 M NaCl wash) is removed and saved; this supernatant contains the soluble form of GMP-140. Care is taken not to remove the top part of the pellet with the supernatant. The pellets are then homogenized in extraction buffer (TBS, 5 mM benzamidine, 5 mM EDTA, pH 7.5, 100 M leupeptin, 2% Triton X-100). After centrifugation at 19,500 rpm for 25 min at 4° C., the supernatant is removed. The extraction procedure is repeated with the pellet and the supernatant is combined with the first supernatant. The combined extracts, which contain the membrane form of GMP-140, are adjusted to 0.5 M NaCl.

The soluble fraction (0.5 M NaCl wash) and the membrane extract (also adjusted to 0.5 M NaCl) are absorbed with separate pools of the monoclonal antibody S12 (directed to human GMP-140) previously coupled to Affigel (Biorad) at 5 mg/ml for 2 h at 4° C. After letting the resins settle, the supernatants are removed. The S12 Affigel containing bound GMP-140 is then loaded into a column and washed overnight at 4° C. with 400 ml of 0.5 M NaCl, 20 mM Tris pH 7.5, 0.01% Lubrol PX.

Bound GMp-140 is eluted from the S12 Affigel with 100 ml of 80% ethylene glycol, 1 mM MES pH 6.0, 0.01% Lubrol PX. Peak fractions with absorbance at 280 nm are pooled. Eluates are dialyzed against TBS with 0.05% Lubrol, then applied to a Mono Q column (FPLC from Pharmacia). The concentrated protein is step eluted with 2 M NaCl, 20 mM Tris pH 7.5 (plus 0.05% Lubrol PX for the membrane fraction). Peak fractions are dialyzed into TBS pH 7.5 (plus 0.05% Lubrol PX for the membrane fraction).

GMP-140 is plated at 5 micrograms/ml and the control proteins: human serum albumin (Alb), platelet glycoprotein IIb/IIIa (IIb), von Willebrand factor (vWF), fibrinogen (FIB), thrombomodulin (TM), gelatin (GEL) or human serum (HS), are added at 50 micrograms/ml. All wells are blocked for 2 h at 22° C. with 300 microliters HBSS containing 10 mg/ml HSA, then washed three times with HBSS containing 0.1% Tween-20 and once with HBSS. Cells ($2 \times 10^5$ per well were added to the wells and incubated at 22° C. for 20 min. The wells were then filled with HBSS/HSA, sealed with acetate tape (Dynatech), and centrifuged inverted at 150 g for 5 min. After discarding nonadherent cells and supernates, the contents of each well are solubilized with 200 microliters 0.5% hexadecyltrimethylammonium bromide, Sigma, in 50 mM potassium phosphate, pH 6.0, and assayed for myeloperoxidase activity, Ley, et al., Blood 73, 1324–1330 (1989). The number of cells bound was derived from a standard curve of myeloperoxidase activity versus numbers of cells. Under all assay conditions, the cells released less than 5% of total myeloperoxidase and lactate dehydrogenase. Results are presented in Table I. 100% adhesion is that seen in the presence of the C-terminal peptide (amino acid residues 761-777 of GMP-140) as a negative control; this value is the same as controls in which neither peptide nor antibody is added to the cells. Inhibition is read as a lower percent adhesion, so that a value of 5% mean that 95% of the specific adhesion was inhibited.

None of the peptides from the EGF domain of GMP-140 inhibited adhesion. However, peptides from three noncontiguous regions of the lectin domain inhibited adhesion. The three regions from the lectin domain are from amino acid 19 to 34, amino acid 54 to 72, amino acid 73 to 89, and an overlapping peptide of amino acids 66-78. Amino acids are numbered based on the number of the residues contained in the peptide, with residue 1 defined as the N terminus of the mature protein after cleavage of the signal peptide.

Currently, the shortest peptide sequences derived from these sequences that are known to have activity range from eight to thirteen amino acids, varying somewhat depending on the area of the lectin domain from it was derived. Some of the shorter peptides have more activity than the longer peptide sequences. The shortest active peptide characterized at this time is lectin domain amino acids 23 to 30, derived from lectin domain amino acids 19 to 34. This peptide is identical among GMP-140, ELAM-1, and the homing receptor with the exception of a single amino acid difference in ELAM-1, and is therefore expected to inhibit cell-cell contacts mediated by all three selectins. The shortest active peptide derived from lectin domain amino acids 54 to 72 known at this time is from amino acid 54 to 63. The shortest active peptide derived from lectin domain amino acids 78-89 known at this time is from amino acids 73 to 83. In addition, an overlapping peptide, spanning amino acids 66 to 78, is very active. It may be possible to design two active shorter, non-overlapping peptides from the region spanning amino acids 66 to 83.

As shown in Table I, some of these regions are more highly conserved among the selectins than others. As a result, it is possible to use peptides derived from the highly conserved regions to modulate interactions involving all of the selectins and peptides from the regions that are less conserved among the selectins to modulate interactions only involving GMP-140. For example, the central core of lectin region 19-34 (residues 23-30) is extraordinarily conserved among the three molecules. In contrast, the amino acid sequence 54 to 60, derived from lectin region 54 to 72, has a number of differences among the selectins.

TABLE I

Comparison of Lectin Domains of GMP-140, ELAM-1, and LEU-8 and Percentage of Neutrophils Bound to GMP-140 in the Presence of GMP-140-derived peptides.

| Protein/Peptide | Amino Acids | | | % Bound[a] |
|---|---|---|---|---|
| | 19 | | 34 | |
| GMP-140 | CQ | NRYTDLVAIQ | NKNE | |
| ELAM-1 | CQ | QRYTHLVAIQ | NKEE | |
| LEU-8 | CR | DNYTDLVAIQ | NKAE | |
| CONSENSUS | Cq | .rYTdLVAIQ | NK.E | |
| GMP-140 peptides | | | | |
| 19-34 | — | ——— | — | 5% |
| 19-26 | — | ——— | | 92% |
| 27-34 | | ——— | — | 91% |
| 19-30 | — | ——— | | 12% |
| 23-34 | | ——— | — | 30% |
| 21-30 | | ——— | | 20% |
| 22-30 | | ——— | | 6% |
| 23-30 | | ——— | | 7% |
| 21-29 | | ——— | | 71% |
| 21-28 | | ——— | | 85% |
| 21-27 | | ——— | | 65% |
| | 54 | | 72 | |
| GMP-140 | RKNNKTW | TWVGTKKALT | NE | |
| ELAM-1 | RKVNNVW | VWVGTQKPLT | EE | |
| LEU-8 | RKIGGIW | TWVGTNKSLT | EE | |
| CONSENSUS | RK.n..w | tWVGT.K.LT | eE | |
| GMP-140 peptides | | | | |
| 54-72 | ——— | ——— | — | 15% |
| 54-63 | ——— | — | | 13% |
| 64-72 | | ——— | — | 92% |
| 54-58 | ——— | | | 108% |
| 59-63 | — | — | | 102% |
| 54-60 | ——— | | | 63% |
| 57-63 | — | — | | 69% |
| 55-60 | ——— | | | 70% |
| 56-60 | ——— | | | 96% |
| 54-59 | ——— | | | 86% |
| | 66 | 73 | 89 | |
| GMP-140 | KKALT | ENAENWADNE | PNNKRNNED | |
| ELAM-1 | QKPLT | EEAKNWAPGE | PNNRQKDED | |
| LEU-8 | NKSLT | EEAENWGDGE | PNNKKNKED | |
| CONSENSUS | .K.LT | eEAeNWadgE | PNNk.n.ED | |
| GMP-140 peptides | | | | |
| 73-89 | | ——— | ——— | 22% |
| 73-80 | | ——— | | 100% |
| 81-89 | | | ——— | 104% |
| 73-85 | | —— | ——— | 41% |
| 77-89 | | —— | ——— | 68% |
| 73-83 | | ——— | — | 17% |
| 66-78 | — | —— | | 6% |

[a]THe number of cells bound to immobilized GMP-140 was determined as described in Geng, et al., Nature 343:757-760 (1990). The number of cells bound in the presence of the control C-terminal peptide (residues 761-777) was normalized to 100%. This value was identical to that observed in the absence of peptide. Peptide inhibition of adhesion is indicated by an adhesion value significantly less than 100%; for example, a value of 5% indicates 95% inhibition of adhesion seen in cont rols. All peptides were added to a final concentration of 1.5 mM.

EXAMPLE 2: DEMONSTRATION OF COMPETITIVE INHIBITION BY PEPTIDES FROM THE LECTIN DOMAIN OF GMP-140 OF THE BINDING OF MONOCLONAL ANTIBODIES TO IMMOBILIZED GMP-140

Example 1 demonstrates that peptides from three regions of the lectin domain of GMP-140 inhibit binding of neutrophils to GMP-140 immobilized on a surface. A study was also done to determine whether the peptides would also inhibit binding of monoclonal antibodies to the immobilized GMP-140.

Three monoclonal antibodies (mAb) that block adhesion of neutrophils to GMP-140 were developed, designated G1, G2, and G3. Based on competitive ELISAs with the purified protein, G1, G2, and G3 each recognize distinct or only partially overlapping epitopes. 1.5 mM peptide was added to biotinylated mAb at a concentration of 2.5 micrograms/ml, which were then added to the wells containing GMP-140, as described in example 1. Binding was measured by an ELISA with an avidin detection system.

The monoclonal antibodies were biotinylated as follows: to 0.5 ml of purified IgG antibody (1 mg/ml in PBS, pH 7.4) was added 50 μl of 3.2 mM N-hydroxysuccinimide biotin in dimethyl sulfoxide and 50 μl of 1 M NaHCO₃. After a 2 hour incubation at room temperature in the dark, the reaction was stopped with 50 μl of 1 M NH₄Cl. The biotinylated antibody was then separated from other components by gel filtration on a PD-10 column equilibrated in PBS. The ELISA was performed as follows; all steps were performed at room temperature.

Biotinylated antibody (2.5 μg/ml) with or without 1.5 mM peptide was incubated with wells coated with GMP-140 as described in example 1. After a 2 hour incubation, the antibody was removed, the wells were washed, and 0.1 ml of horseradish peroxidase-conjugated stepavidin (Pierce), diluted 1:1000 in HBSS/HSA, was added for 30 min. The wells were then washed and 0.1 ml of peroxidase substrate (Pierce) was added for 15 min. The color reaction was read at 405 nm.

The results are shown in Table 2.

TABLE 2

Effect of soluble peptides on binding of biotinylated monoclonal antibodies to immobilized GMP-140.

| PEPTIDES[a] | % Binding of Biotinylated MAbs[b] | | |
|---|---|---|---|
| | G1 | G2 | G3[c] |
| LECTIN 19-34 | 23 | 26 | 24 |
| LECTIN 19-30 | | | 54 |
| LECTIN 54-72 | 106 | 125 | 104 |
| LECTIN 73-89 | 95 | 99 | 94 |
| LECTIN 91-108 | 97 | 93 | 96 |
| LECTIN 110-116 | 98 | 100 | 108 |
| LECTIN/EGF 118-126 | 92 | 92 | 104 |
| EGF 128-132 | 107 | 92 | 104 |
| EGF 134-141 | 97 | 104 | 109 |
| EGF 145-158 | 94 | 92 | 108 |
| REPEATS 544-556 | 107 | 96 | 111 |
| TRANSMEMBRANE 755-761 | 100 | 119 | 104 |
| SECRETORY 720-721/762-765 | 106 | 99 | 104 |
| C-TERMINUS 761-777 | 100 | 100 | 100 |

[a]The peptide (1.5 mM) was added to the mAb (2.5 micrograms/ml) prior to addition of the solution to the microtiter well containing immobilized GMP-140.
[b]Binding of the biotinylated mAb G1, G2, or G3 to immobilized GMP-140 was measured by ELISA with an avidin detection system.
[c]G1, G2, and G3 are antibodies binding to GMP-140 that prevent neutrophil adhesion to immobilized GMP-140.

EXAMPLE 3: CHARACTERIZATION OF THE "LIGAND" OR "COUNTER-RECEPTOR" FOR GMP-140 AND INTERACTION WITH GMP-140 PEPTIDES

The ability of the lectin 19-34 peptide to prevent binding to GMP-140 of all three monoclonal antibodies that block interactions of GMP-140 with leukocytes provides additional proof of the importance of the lectin domain in leukocyte recognition. It is postulated from this data that the conformation of the lectin domain is modulated by interactions with the EGF domain; these interactions in turn are modulated by divalent cations, which may bind to both the lectin and EGF domains. The result is a three-dimensional conformation of the lectin domain that confers affinity and specificity of binding to its receptor(s) on neutrophils and monocytes.

This receptor is believed to be a glycoprotein containing sialic acid and other oligosaccharides that are recognized by the lectin domain of GMP-140. Using the assay described in example 1, and an assay in which $^{125}$I[GMP-140] binds specifically, saturably and reversibly to human neutrophils, as described by Moore and McEver, Clin.Res. 38, 364A (1990), certain critical structural features of the ligand (or, perhaps more accurately, "counter-receptor") for GMP-140 on human neutrophils have been defined.

Neutrophils were treated with proteases, either trypsin or elastase, to determine if the receptor contains a protease-sensitive protein component. Greater than 70% of the adhesion of neutrophils to immobilized GMP-140 was abolished by the proteases, but not by elastase or trypsin inactivated with diisopropylfluorophosphate, indicating that at least a substantial fraction of the leukocyte counter-receptors for GMP-140 contain a protease-sensitive protein component.

Treatment of neutrophils with neuraminidase purified from Vibrio cholera abolished both binding of $^{125}$[GMP-140] to human neutrophils and adhesion of neutrophils to immobilized GMP-140, indicating that sialic acid residues constitute an essential component of the leukocyte counter-receptor(s) for GMP-140.

A monoclonal antibody to the Lewis X antigen, Lacto-N-fucopentaose III, "LNF-III", blocked binding of $^{125}$[GMP-140] to human neutrophils in a dose-dependent fashion, indicating that LNF-III, a repeating structure found in polylactosaminoglycans of neutrophils and monocytes, is a component of the leukocyte counter-receptor(s) for GMP-140.

These results indicate that the counter-receptor, or ligand, on leukocytes for GMP-140 is a glycoprotein wherein a combination of sialic acid and LNF-III are required for receptor function. The predominant polyfucosylated lactosaminoglycan on human granulocytes is a tretraantennary structure. As described by Spooncer, et al., J. Biol. Chem. 259, 4792-4801 (1984), this structure contains four linear polylactosaminoglycan chains attached to core mannose residues of complex oligosaccharides, which are attached to asparagine residues of core proteins. Only one of these four chains is modified by both fucose and sialic acid, as reported by Fukuda, et al., J. Biol. Chem. 259, 10925-10935 (1984). This chain is linked by a $\beta \to 6$ linkage to the core mannose. This chain is terminated by a sialic acid linked $\alpha 2 \to 3$ to a galactose which is part of an LNF-III unit. As shown by Fukuda, et al., (1984), the structure is:

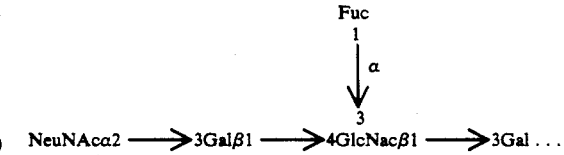

It has not been determined whether the sialyated form of LNF-III operates within the context of the larger tetraantennary oligosaccharide, which can have minor variations, or the combination within the context of a core protein. Since fucosylated polylactosaminoglycans are also found on glycolipids of neutrophils and monocytes, as reported by Spooncer, et al., (1984), and proteases do not block all GMP-140 binding, it is possible that some of the GMP-140 may be interacting with oligosaccharides that form part of glycolipids. Conversely, a role for direct protein-protein interactions between GMP-140 and protein components of the glycoprotein receptor cannot be excluded.

The three peptide regions of the lectin domain interact with the leukocyte counter-receptor. When presented in the three-dimensional context of the lectin domain of the native protein, the three regions bind cooperatively with precise specificity and high affinity to the appropriate receptor. However, each region is sufficient to competitively inhibit leukocyte binding to GMP-140 alone. As a result, it is possible to use peptides containing one or more of these regions, alone or in combination with additional or substituted amino acids, to modulate binding of leukocytes, platelets and endothelial cells via GMP-140.

EXAMPLE 4: EFFECT OF CONCENTRATION ON PEPTIDE INHIBITION OF BINDING OF NEUTROPHILS TO IMMOBILIZED GMP-140

Peptides from the lectin-like domain of GMP-140 were assayed for their ability to inhibit adhesion of neutrophils to immobilized GMP-140 in the assay described in example 1. Concentrations tested ranged from 0.1 mM to 1.5 mM.

Figure 3:
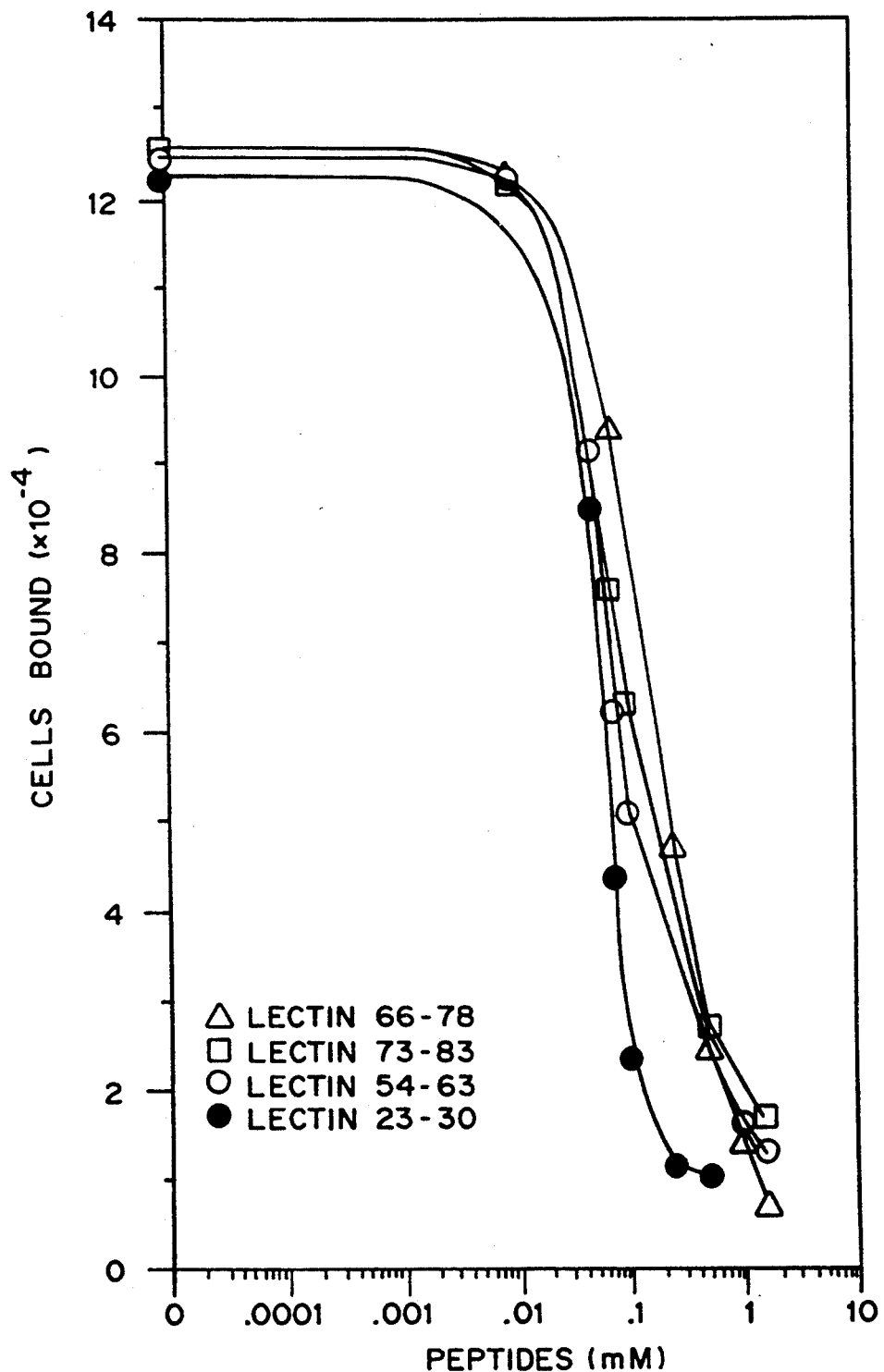
FIG. 3 is a graph demonstrating inhibition of binding by peptides from the GMP-140 lectin domain, amino acids 66–78 (triangle), amino acids 73–83 (square), amino acids 54–63 (circle), and amino acids 23–30 (dark circle), comparing number of cells bound to mM of peptides.

The results for four peptides are shown in FIG. 3. It is apparent that the peptides from the GMP-140 lectin domain, amino acids 66–78, amino acids 73–83, amino acids 54–63, and amino acids 23–30, inhibited binding in a dose-dependent manner. The $IC_{50}$, the dose of peptide required to inhibit adhesion by 50%, ranges from about 50 μM to about 300 μM, depending on the peptides. These ranges are well within the effective concentrations for the in vivo administration of peptides, based on comparison with the RGD-containing peptides, described, for example, in U.S. Pat. No. 4,792,525 to Ruoslaghti, et al., used in vivo to alter cell attachment and phagocytosis.

EXAMPLE 5: MODIFICATION OF PEPTIDES AND COMPARISON OF ADHESION POTENCY WITH GMP-140

In some cases, modification of the peptides by alteration of the amino acids themselves or by attachment to a carrier molecule is required to increase half-life of the molecule in vivo.

Lectin peptide 19–34 was conjugated to the carrier protein keyhole limpet hemocyanin by its N-terminal cysteine by standard procedures such as the commercial Imject kit from Pierce Chemicals. This peptide-KLH conjugate was then tested in the assay described in example 1 and the numbers of cells bound determined.

Figure 4A:
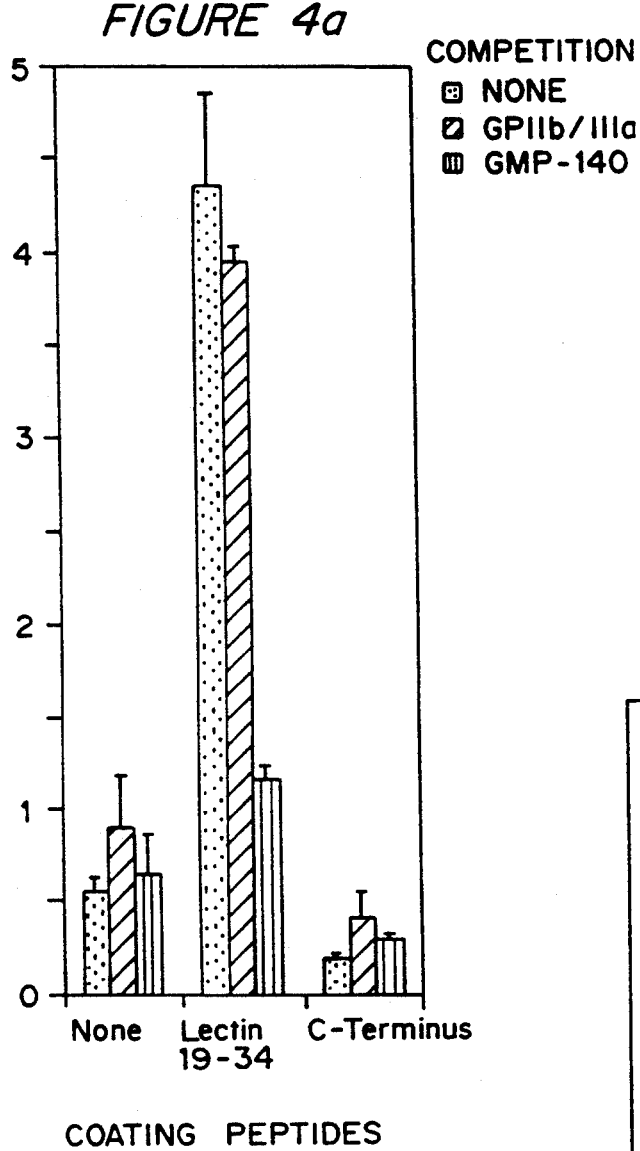
FIG. 4A and B are comparisons of the specific adhesion of neutrophils to microtiter wells coated with no peptide (1); coated with lectin domain peptide 19-34 conjugated to KHL (2); or coated with a control carboxyterminus peptide (amino acid residues 761-777) conjugated to KLH (3), blocked with Hank's Balanced Salt Solution containing human serum albumin prior to addition of $2 \times 10^5$ neutrophils to each well, in the presence of fluid-phase competitors. Fluid-phase competitors added to the neutrophils prior to transfer to the wells were: Panel A, none (dark bar), purified platelet glycoprotein IIb-IIIa (slashed bar), or purified GMP-140 (stippled bar); Panel B, none (dark bar), 1.5 mM C-terminal peptide 761-777 (slashed bar), 1.5 mM lectin domain peptide 19-34 (stippled bar).
Figure 4B:
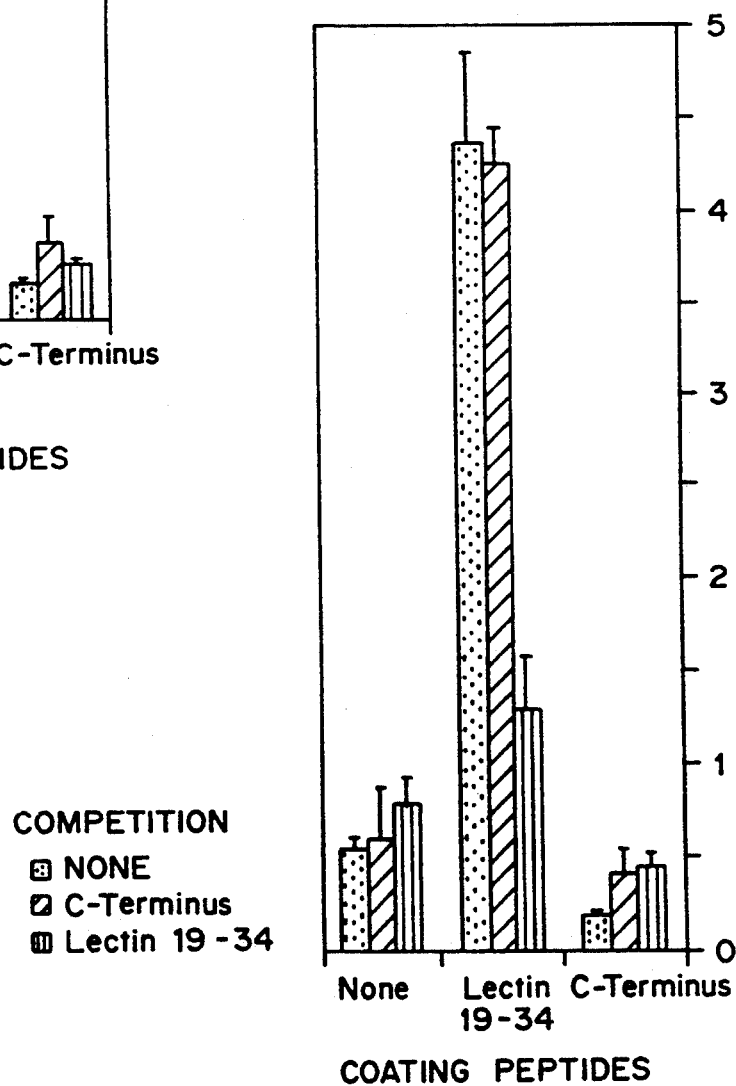

FIG. 4A and B are comparisons of the specific adhesion of neutrophils to microtiter wells coated with no peptide (1); coated with lectin domain peptide 19–34 conjugated to KHL (2); or coated with a control carboxyterminus peptide (amino acid residues 761–777) conjugated to KLH (3), blocked with Hank's Balanced Salt Solution containing human serum albumin prior to addition of $2 \times 10^5$ neutrophils to each well, in the presence of fluid-phase competitors. Fluid-phase competitors added to the neutrophils prior to transfer to the wells were none (control), purified platelet glycoprotein IIb-IIIa (control), or purified GMP-140 (Panel A); or none (control), 1.5 mM C-terminal peptide 761–777 (control), 1.5 mM lectin domain peptide 19–34 (Panel B).

It is apparent from the graphs that the lectin peptide-KHL conjugate, when immobilized on plastic, directly supports neutrophil adhesion, although not as efficiently as native GMP-140. For purposes of comparison, when 200,000 neutrophils are added to a well, the lectin peptide 19–34 binds 40,000 and GMP-140 binds 120,000. The peptide is coupled to KLH simply to facilitate its coating to plastic. The ability to compete for adhesion with fluid-phase purified GMP-140 and the lectin peptide 19–134, but not with other proteins or peptides, shows that the adhesion is specific. In other studies, a large number of peptides from other regions of the lectin domain, the EGF domain, and scattered regions of GMP-140 do not inhibit neutrophil adhesion to immobilized GMP-140.

PREPARATION OF DIAGNOSTIC AND THERAPEUTIC AGENTS FROM PEPTIDES DERIVED FROM THE LECTIN DOMAIN OF GMP-140

The peptides described above have a variety of applications as diagnostic reagents and, potentially, in the treatment of numerous inflammatory disorders.

DIAGNOSTIC REAGENTS

The GMP-140 binding peptides can also be used for the detection of human disorders in which GMP-140 ligands might be defective. Such disorders would most likely be seen in patients with increased susceptibility to infections in which leukocytes might not be able to bind to activated platelets or endothelium. Cells to be tested, usually leukocytes, are collected by standard medically approved techniques and screened. Detection systems include ELISA procedures, binding of radiolabeled antibody to immobilized activated cells, flow cytometry, or other methods known to those skilled in the arts. Inhibition of binding in the presence and absence of the lectin domain peptides can be used to detect defects or alterations in selectin binding. Such disorders would most likely be seen in patients with increased susceptibility to infections in which leukocytes would have defective binding to platelets and endothelium because of deficient leukocyte ligands for GMP-140. The GMP-140 peptide is labeled radioactively, with a fluorescent tag, enzymatically, or with electron dense material such as gold for electron microscopy. The cells to be examined, usually leukocytes, are incubated with the labeled GMP-140 peptides and binding assessed by methods described above with antibodies to GMP-140, or by other methods known to those skilled in the art. If ligands for GMP-140 are also found in the plasma, they can also be measured with standard ELISA or radioimmunoassay procedures, using labeled GMP-140 peptide instead of antibody as the detecting reagent.

A similar approach can be used to determine qualitative or quantitative disorders of GMP-140 itself. In this case, sialyated LNF-III oligosaccharides, or appropriate derivatives thereof, are labeled and tested for their ability to bind to GMP-140 on activated platelets from patients with disorders in which GMP-140 might be defective.

CLINICAL APPLICATIONS

Since GMP-140 has several functions related to leukocyte adherence, inflammation, and coagulation, clinically, compounds which interfere with binding of GMP-140 and/or the other selectins, including ELAM-1 and LEU-8, such as the GMP-140 peptides, can be used to modulate these responses.

For example, GMP-140 peptides can be used to competitively inhibit leukocyte adherence by competitively binding to GMP-140 receptors on the surface of leukocytes. This kind of therapy would be particularly useful in acute situations where effective, but transient, inhibition of leukocyte-mediated inflammation is desirable. Chronic therapy by infusion of GMP-140 peptides may also be feasible in some circumstances.

Since GMP-140 is believed to stabilize irreversible platelet aggregates after initial cell-cell contact is initiated by binding of adhesive proteins to GPIIb-IIIa, inhibition of this interaction could enhance the ability of competitive antagonists of the GPIIb-IIIa-adhesive protein interaction to block platelet aggregation. An example of a clinical situation where this might be useful would be in the respiratory distress syndrome, tumor metastasis, rheumatoid arthritis and atherosclerosis.

Reperfusion injury is a major problem in clinical cardiology. Therapeutic agents that reduce leukocyte adherence in ischemic myocardium can significantly enhance the therapeutic efficacy of thrombolytic agents. Thrombolytic therapy with agents such as tissue plasminogen activator or streptokinase can relieve coronary artery obstruction in many patients with severe myocardial ischemia prior to irreversible myocardial cell death. However, many such patients still suffer myocardial neurosis despite restoration of blood flow. This "reperfusion injury" is known to be associated with adherence of leukocytes to vascular endothelium in the ischemic zone, presumably in part because of activation of platelets and endothelium by thrombin and cytokines that makes them adhesive for leukocytes (Romson et al., *Circulation* 67: 1016–1023, 1983). These adherent leukocytes can migrate through the endothelium and destroy ischemic myocardium just as it is being rescued by restoration of blood flow.

There are a number of other common clinical disorders in which ischemia and reperfusion results in organ injury mediated by adherence of leukocytes to vascular surfaces, including strokes; mesenteric and peripheral vascular disease; organ transplantation; and circulatory shock (in this case many organs might be damaged following restoration of blood flow).

Bacterial sepsis and disseminated intravascular coagulation often exist concurrently in critically ill patients. They are associated with generation of thrombin, cytokines, and other inflammatory mediators, activation of platelets and endothelium, and adherence of leukocytes and aggregation of platelets throughout the vascular system. Leukocyte-dependent organ damage is an important feature of these conditions.

Adult respiratory distress syndrome is a devastating pulmonary disorder occurring in patients with sepsis or following trauma, which is associated with widespread adherence and aggregation of leukocytes in the pulmonary circulation. This leads to extravasation of large amounts of plasma into the lungs and destruction of lung tissue, both mediated in large part by leukocyte products.

Two related pulmonary disorders that are often fatal are in immunosuppressed patients undergoing allogeneic bone marrow transplantation and in cancer patients suffering from complications that arise from generalized vascular leakage resulting from treatment with interleukin-2 treated LAK cells (lymphokine-activated lymphocytes). LAK cells are known to adhere to vascular walls and release products that are presumably toxic to endothelium. Although the mechanism by which LAK cells adhere to endothelium is not known, such cells could potentially release molecules that activate endothelium and then bind to endothelium by mechanisms similar to those operative in neutrophils.

Tumor cells from many malignancies (including carcinomas, lymphomas, and sarcomas) can metastasize to distant sites through the vasculature. The mechanisms for adhesion of tumor cells to endothelium and their subsequent migration are not well understood, but may be similar to those of leukocytes in at least some cases. The association of platelets with metastasizing tumor cells has been well described, suggesting a role for platelets in the spread of some cancers.

Platelet-leukocyte interactions are believed to be important in atherosclerosis. Platelets might have a role in recruitment of monocytes into atherosclerotic plaques; the accumulation of monocytes is known to be one of the earliest detectable events during atherogenesis. Rupture of a fully developed plaque may not only lead to platelet deposition and activation and the promotion of thrombus formation, but also the early recruitment of neutrophils to an area of ischemia.

Another area of potential application is in the treatment of rheumatoid arthritis.

In these clinical applications, the peptide, or mixture of peptides, in an appropriate pharmaceutical carrier, is preferably administered intravenously where immediate relief is required. The peptide(s) can also be administered intramuscularly, intraperitoneally, subcutaneously, orally, as the peptide, conjugated to a carrier molecule, or in a drug delivery device. The peptides can additionally be modified chemically to increase their in vivo half-life.

The peptides can be prepared by proteolytic cleavage of GMP-140, or, preferably, by synthetic means such as those used to prepare the peptides in example 1. These methods are known to those skilled in the art. An example is the solid phase synthesis described by J. Merrifield, *J. Am. Chem. Soc.* 85, 2149 (1964), used in U.S. Pat. No. 4,792,525, and described in U.S. Pat. No. 4,244,946, wherein a protected alpha-amino acid is coupled to a suitable resin, to initiate synthesis of a peptide starting from the C-terminus of the peptide. Other methods of synthesis are described in U.S. Pat. Nos. 4,305,872 and 4,316,891. These methods can be used to synthesize peptides having identical sequence to GMP-140, or substitutions or additions of amino acids, which can be screened for activity as described in examples 1 to 3.

The peptide can also be administered as a pharmaceutically acceptable acid- or base- addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Peptides containing cyclopropyl amino acids, or amino acids derivatized in a similar fashion, can also be used. These peptides retain their original activity but have increased half-lives in vivo. Methods known for modifying amino acids, and their use, are known to those skilled in the art, for example, as described in U.S. Pat. No. 4,629,784 to Stammer.

Peptides that are biologically active are those which inhibit binding of neutrophils and monocytes to GMP-140, or which inhibit leukocyte adhesion to endothelium that is mediated by ELAM-1 and/or the homing receptor. Sialyated LNF-III oligosaccharides that are active can be screened in a similar manner.

Suitable pharmaceutical vehicles are also known to those skilled in the art. For parenteral administration, the peptide will usually be dissolved or suspended in sterile water or saline. For enteral administration, the peptide will be incorporated into an inert carrier in tablet, liquid, or capsular form. Suitable carriers may be starches or sugars and include lubricants, flavorings, binders, and other materials of the same nature. The GMP-140 peptide can also be administered locally at a wound or inflammatory site by topical application of a solution or cream.

Alternatively, the peptide may be administered in liposomes or microspheres (or microparticles). Methods for preparing liposomes and microspheres for administration to a patient are known to those skilled in the art. U.S. Pat. No. 4,789,734 describe methods for encapsulating biological materials in liposomes. Essentially, the material is dissolved in an aqueous solution, the appropriate phospholipids and lipids added, along with surfactants if required, and the material dialyzed or sonicated, as necessary. A good review of known methods is by G. Gregoriadis, Chapter 14. "Liposomes", *Drug Carriers in Biology and Medicine* pp. 287–341 (Academic Press, 1979). Microspheres formed of polymers or proteins are well known to those skilled in the art, and can be tailored for passage through the gastrointestinal tract directly into the bloodstream. Alternatively, the peptide can be incorporated and the microspheres, or composite of microspheres, implanted for slow release over a period of time, ranging from days to months. See, for example, U.S. Pat. Nos. 4,906,474, 4,925,673, and 3,625,214.

The subject peptides are generally active when administered parenterally in amounts above about 1 μg/kg of body weight. For treatment of most inflammatory disorders, the dosage range will be between 0.1 to 30 mg/kg of body weight. A dosage of 70 mg/kg may be required for some of the peptides characterized in the examples. This dosage will be dependent, in part, on whether one or more peptides are administered. As discussed with respect to binding of the three regions of the lectin domain, a synergistic effect may be seen with combinations of peptides from different, or overlapping, regions of the lectin domain, or in combination with peptides derived from the EGF domain of GMP-140.

The peptides can also be coated onto substrates for use as prosthetics that are implanted into the body to prevent leukocyte adhesion to platelets or endothelium.

The criteria for assessing response to therapeutic modalities employing antibodies to GMP-140 is dictated by the specific condition and will generally follow standard medical practices. For example, the criteria for the effective dosage to prevent extension of myocardial infarction would be determined by one skilled in the art by looking at marker enzymes of myocardial necrosis in the plasma, by monitoring the electrocardiogram, vital signs, and clinical response. For treatment of acute respiratory distress syndrome, one would examine improvements in arterial oxygen, resolution of pulmonary infiltrates, and clinical improvement as measured by lessened dyspnea and tachypnea. For treatment of patients in shock (low blood pressure), the effective dosage would be based on the clinical response and specific measurements of function of vital organs such as the liver and kidney following restoration of blood pressure. Neurologic function would be monitored in patients with stroke. Specific tests are used to monitor the functioning of transplanted organs; for example, serum creatinine, urine flow, and serum electrolytes in patients undergoing kidney transplantation.

Modifications and variations of the present invention, methods for modulating binding reactions involving GMP-140, will be obvious to those skilled in the art from the foregoing detailed description. Such modifications and variations are intended to come within the scope of the appended claims.

I claim:

1. An isolated peptide between eight amino acids and 118 amino acids in length comprising an amino acid sequence selected from the group consisting of C $X_1$ $X_2$ $X_3$ Y T $X_4$ L V A I Q N K $X_5$ E,
C $X_1$ $X_2$ $H_2$ Y T $X_4$ L V A I Q,
Y T $X_4$ L V A I Q N K $X_5$ E,
$X_2$ $X_3$ Y T $X_4$ L V A I Q,
$X_3$ Y T $X_4$ L V A I Q,
Y T $X_4$ L V A I Q,
R K $X_6$ $X_7$ $X_8$ $X_9$ W $X_{10}$ W V. G T $X_{11}$ K $X_{12}$ L T $X_{13}$ E,
R K $X_6$ $X_7$ $X_8$ $X_9$ W $X_{10}$ W V,
$X_{11}$ K $X_{12}$ L T $X_{13}$ E A $X_{14}$ N W $X_{15}$ $X_{16}$,
A $X_{14}$ N W $X_{15}$ $X_{16}$ $X_7$ E P N N $X_{17}$ $X_{18}$ $X_{19}$ $X_{20}$ E D,
A $X_{14}$ N W $X_{15}$ $X_{16}$ $X_7$ E P N N,
A $X_{14}$ N W $X_{15}$ $X_{16}$ $X_7$ E P N N $X_{17}$ $X_{18}$,
and $X_{15}$ $X_{16}$ $X_7$ E P N N $X_{17}$ $X_{18}$ $X_{19}$ $X_{20}$ E D, wherein
$X_1$ = Q or R;
$X_2$ = N, Q, or D;
$X_3$ = R or N;
$X_4$ = D or H;
$X_5$ = N, E or A;
$X_6$ = N, V, or I;
$X_7$ = N or G;
$X_8$ = K, N, or G;
$X_9$ = T, V, or I;
$X_{10}$ = T or V;
$X_{11}$ = K, Q, or N;
$X_{12}$ = A, P, or S;
$X_{13}$ = N or E;
$X_{14}$ = E or K;
$X_{15}$ = A or G;
$X_{16}$ = D or P;
$X_{17}$ = K or R;
$X_{18}$ = R, Q, or K;
$X_{19}$ = N or K;
$X_{20}$ = N, D, or K;

and the peptide inhibits binding of neutrophils and monocytes to GMP-140.

2. The peptide of claim 1 wherein the amino acid sequence is selected from the group consisting of CQNRYTDLVAIQNKNE, AENWADNEPNNKRNNED, RKNNKTWTWVGTKKALTNE, and KKALTNEAENWAD.

3. The peptide of claim 1 wherein the amino acid sequence is selected from the group of lectin domain peptides amino acids 19–34, 19–30, 23–34, 21–30, 22–30, 23–30, 54–72, 54–63, 66–78, 73–89, 73–83, 73–85, 77–89.

4. A peptide conjugate comprising the peptide of claim 1 bound to a carrier molecule.

5. A prosthetic comprising the peptide of claim 1 bound to an inert substrate for implantation in the body.

6. A pharmaceutical composition comprising the peptide of claim 1 in a pharmaceutical carrier acceptable for administration to a patient.

7. A diagnostic comprising the peptide of claim 1 further comprising a detectable label selected from the group consisting of fluorescent, radioactive, and enzymatic labels.

* * * * *